United States Patent [19]

Pak

[11] Patent Number: 4,921,807

[45] Date of Patent: May 1, 1990

[54] METHOD AND APPARATUS FOR MAINTAINING URINE SPECIMENS

[75] Inventor: Charles Y. C. Pak, Dallas, Tex.

[73] Assignee: Mission Pharmacal Company, San Antonio, Tex.

[21] Appl. No.: 148,148

[22] Filed: Jan. 26, 1988

Related U.S. Application Data

[63] Continuation of Ser. No. 787,059, Oct. 15, 1985, abandoned.

[51] Int. Cl.$^5$ .............................................. G01N 1/28
[52] U.S. Cl. ........................................ 436/18; 436/8; 436/74; 436/108; 436/129; 436/176; 436/61; 435/10; 435/12; 422/99; 116/209; 514/970
[58] Field of Search .................. 436/8, 18, 74, 108, 436/129, 176, 61; 435/10, 12; 424/99; 574/970; 116/209

[56] References Cited

U.S. PATENT DOCUMENTS

| | | | |
|---|---|---|---|
| 2,504,299 | 4/1950 | Cartwright | 116/202 |
| 3,534,851 | 10/1970 | Peterson et al. | 436/18 |
| 3,916,014 | 10/1975 | Nishihara et al. | 568/746 |
| 3,931,340 | 1/1976 | Nishihara et al. | 568/746 |
| 4,034,609 | 7/1977 | Fuller | 73/73 |
| 4,042,337 | 8/1977 | Griffith | 422/102 |
| 4,200,651 | 4/1980 | Griffith | 514/625 |
| 4,203,967 | 5/1980 | Gallo-Torres | 424/9 |
| 4,461,829 | 7/1984 | Greenquist | 422/56 |

OTHER PUBLICATIONS

Windholy, ed., *The Merck Index*, 10th ed., Merck & Co, Inc. (Rahway) 1983, pp. 185 and 1347.
Sonnenwirth, ed., *Gradwohl's Clinical Laboratory* Methods and Diagnosis, 8th ed., C. V. Mosby Co. (St. Louis) 1980, pp. 150–151.

*Primary Examiner*—Barry S. Richman
*Assistant Examiner*—Timothy M. McMahon
*Attorney, Agent, or Firm*—Ross, Howison, Clapp & Korn

[57] ABSTRACT

A urine specimen is preserved from bacterial deterioration as to relative constituents by adding thymol. To the thymol-treated specimen, lithium-solution volume-marker is added, then is divided into two (first and second) separate portions. Thereupon, using the first portion, standard conventional measurements and/or analysis is conducted for total volume, pH/acidity, uric acid, citrate, sodium, and potassium. To the second portion, there is added boric acid and hydrochloric acid, followed by standard/conventional measurement and/or analysis for ammonium ion, citrate, calcium, magnesium, phosphorus, oxalate and sulfate. Thereafter the findings are charted and compared to controls.

57 Claims, No Drawings

METHOD AND APPARATUS FOR MAINTAINING URINE SPECIMENS

RELATED APPLICATIONS

This is a continuation of application Ser. No. 06/787,059 filed Oct. 15, 1985, now abandoned.

BACKGROUND OF THE INVENTION

It is now known that kidney stones form from a variety of metabolic, environmental and physicochemical disturbances. Metabolic factors include hypercalciuria (high urinary calcium), hyperoxaluria (high urinary oxalate), hyperuricosuria (high urinary uric acid), hypocitraturia (low urinary citrate), and unusually acid or alkaline urinary medium (Pak, Cecil Textbook of Medicine, 17th Edition, pp. 628–633, 1985). Important environmental factors are low urine volume, high urinary sodium, high urinary sulfate, high urinary phosphate, and low urinary magnesium (Pak et al. J. Urology, October, 1985, in press). Physicochemical factors indicate whether urine samples are supersaturated (therefore likely to support stone formation) with respect to stone-forming salts (calcium oxalate, brushite, sodium urate, struvite and uric acid).

It is presumed that metabolic factors are due to disturbed metabolism of patients suffering from stones, whereas environmental factors originate from dietary aberrations. Physicochemical factors are dependent upon metabolic and environmental factors, since urinary saturation is calculated from various urinary excretions.

Although the measurement of above stone-forming factors/risks would be very helpful in making the appropriate diagonsis and in offering proper treatment, it has been hampered by the difficulty in adequately preserving and collecting urine samples and by the lack of an easily understood way of displaying results.

Thus, there is considerable uncertainty regarding exact methods for preserving urine which would not influence various analyses. It has been suggested that urine samples need to be acidified in order to prevent precipitation of calcium and magnesium salts, and allow proper determination of calcium, magnesium, phosphate and oxalate. Unfortunately, urinary acidification does not allow measurement of pH and uric acid, the latter due to its precipitation in an acid environment. Moreover, considerable care must be taken in adding acidic solution to urine, a task not enjoyed by patients. Freezing may prevent bacterial contamination and may preserve some urinary components (such as citrate). However, precipitation of uric acid and calcium salts may occur when samples are frozen; such precipitates are often hard to redissolve upon thawing. When samples are kept at 20° C. or higher, there may be an incomplete recovery of citrate, pyrophosphate, uric acid and creatinine (due to bacterial contamination and ensuing bacterial enzymatic degradation). In contrast, oxalate content may well increase because it would be formed from ascorbic acid normally contained in urine. Thus, non-refrigerated urine samples may yield lower values for oxalate. The addition of appropriate antibiotics or disinfectants to control bacterial contamination may be helpful, but is not likely to prevent conversion of vitamin C to oxalate or precipitation of stone-forming salts. If urine samples are refrigerated during collection until the time of analysis (within three days of analysis), the urinary composition is maintained, except in few samples which are infected or overly concentrated. However, this procedure is impractical except in the setting of a research center.

Another problem in submitting urine samples for analysis of stone-forming risks to the laboratory is the need to measure total volume (usually 24-hour) accurately. Since shipping 24-hour collection is impractical, it would be advantageous to have total volume of urine measured so that small aliquot(s) of whole urine collection could be sent to the laboratory. Unfortunately, few patients have means to accurately measure urine volume.

Thus, a method of urine collection and preservation, which does not require refrigeration or determination of total volume, permitting accurate analysis of all stone-forming risks previously enumerated from aliquots of urine submitted, is clearly needed.

Even when metabolic and environmental factors could be accurately measured from proper urine collection and preservation system, such information would have a limited value to the physician taking care of the patient unless comparison with normal control value is provided, physicochemical factors are derived, and unless that information is displayed in a readily understandable fashion.

SUMMARY OF THE INVENTION

The invention embodies two parts; first, a reliable method of urine collection and preservation, and second, a graphic display of stone-forming risks. Urine sample is collected in a container containing thymol (to prevent bacterial contamination) and lithium (volume marker). After collection, a small aliquot is transferred to a container with boric acid-hydrochloric acid (to solubilize sparingly soluble calcium and magnesium salts and to prevent vitamin C conversion to oxalate). Another small aliquot is transferred to a container without any boric acid-hydrochloric acid preservation (for the accurate measurement of pH and uric acid without interference by added acid). Thus, the aliquot containing thymol and lithium is analyzed for total volume, pH, uric acid, citrate, sodium and potassium. The other aliquot containing thymol, lithium, hydrochloric acid and boric acid is analyzed for remaining constituents (ammonium, citrate, calcium, magnesium, phosphorus, oxalate and sulfate). (Citrate may be analyzed in either aliquot).

For preserving the urine specimen, the thymol is added in an amount ranging between about 300 mg to about 2000 mg (i.e., 2 g) to one whole day's sample of urine (24-hour sample), preferably from about 600 mg to about 1200 mg (i.e., 1.2 g), a whole day's sample ranging from 0.5 to 4 liters normally, usually from about 1 liter to 2 liters, exact weight of thymol not being critical.

Lithium, in the preferred form of lithium chloride, is added in an amount ranging from 0.375 g to about 10 g to a 24-hour urine sample which also contains thymol. A preferred range is about 1 g to 3 g per total volume of urine collected over one whole day. A less desirable alternate volume-marker is tritium use of which requires radioisotope counting.

After collecting one whole day's urine in a container with thymol and lithium in the above specified amounts, a small portion is taken out without further preservation for the analysis of total volume (amount of urine produced in a day), pH, uric acid, citrate, sodium and potassium. To the second portion, the hydrochloric acid is added in an amount ranging from about 0.5 ml to about 2 ml of concentrated hydrochloric acid per 30 ml of thymol and lithium chloride-treated urine specimen, preferably about 1 ml per 30 ml of the treated specimen. Equivalently the hydrochloric acid may be added as 6N (normal) hydrochloric acid, broad range being about 1 ml to about 4 ml per 30 ml of the treated specimen, preferably from about 2 ml to about 4 ml per 30 ml of the thymol and lithium chloride-treated specimen.

The boric acid is employed in an amount ranging from about 0.3 g to about 1 g per 30 ml of thymol, lithium and hydrochloric acid-treated urine specimen, typically about 0.6 g, the preferred range being from about 0.4 g to about 0.7 g per 30 ml of treated urine specimen. This portion, containing thymol, lithium, hydrochloric acid and boric acid, is analyzed for ammonium, citrate, calcium, magnesium, phosphorus, oxalate and sulfate.

From above urinary measures, the urinary saturation of stone-forming salts is determined using a computer program (Pak et al. J. Lab. Clin. Med. 89: 819–901, 1977 in public domain). Using normal values established by inventors, each urinary measure obtained from the patient can be assigned relative risk (increased risk or reduced risk) for stone formation. The second aspect of this invention embodies a scheme for graphic display of risk factors (metabolic, environmental, physicochemical) which allows a ready visual recognition of important risk factors presumed to cause stone formation (Pak et al. J. Urology, October, 1985).

DETAILED DESCRIPTION OF PREFERRED EMBODIMENTS

Thymol is critical to the present invention there being no know alternatives, other than perhaps related substituted forms thereof—intended to be included within the scope of the invention. However one example of the criticality of the thymol is the fact that acetohydroxamic acid, as a possible alternative preservation, does not completely prevent bacterial contamination and infection in a urine specimen. Likewise chloroforms proved unacceptable because major evaporation took place during storage. Formaldehyde is likewise unsuitable because it reduces pH and interferes with uric acid analysis by uricase technique.

Likewise lithium is a critical volume-marker, as opposed to other tested volume-markers which proved unsatisfactory. For example, copper-soluble salt solutions are not acceptable because they interfere with oxalate determination. Likewise FDC blue-dye was found to be undependable, depending on pH for its color generation.

The method for urine collection and preservation of this invention was derived from extensive laboratory studies by the inventor.

In order to show the effect of the lack of urine preservation on urinary metabolic and environmental risk factors, 10 urine samples were purposely inoculated with bacteria (*E. coli*, proteus-mirabilis and pseudomonas aeruginosa), incubated at 37 degrees centigrade for 24 hours, heated to 70 degrees centigrade and then left at room temperature for 24 hours. Results were compared with those of corresponding aliquots which had been kept refrigerated (fresh) (Table 1).

TABLE 1

| Effect of Bacterial Contamination and Heating | | |
|---|---|---|
| | Fresh | Unpreserved |
| pH | 6.62 ± 0.33 | 8.10 ± 1.01+ |
| Uric Acid (mg/l) | 209 ± 89 | ± 42* |
| Na (meq/l) | 76 ± 26 | 72 ± 25 |
| K (meq/l) | 37 ± 13 | 41 ± 16 |
| NH4 (mg/l) | 102 ± 45 | 637 ± 418+ |
| Citrate (mg/l) | 201 ± 109 | 159 ± 99* |
| Calcium (mg/l) | 59.3 ± 28.0 | 23.6 ± 20.6+ |
| Magnesium (mg/l) | 38.7 ± 13.5 | 12.5 ± 16.4+ |
| Phosphorus (mg/l) | 375.5 ± 101.4 | 317.5 ± 75.2** |
| Oxalate (mg/l) | 13.2 ± 4.7 | 19.3 ± 8.0** |
| Sulfate (mmoles/l) | 10.9 ± 4.3 | 10.4 ± 4.3 |

Significant difference from fresh samples, determined by paired t-test, is given by * for $p < 0.05$, ** $p < 0.01$ and + for $p < 0.001$. Values are presented as mean ± SD.

Thus, samples which were contaminated and non-refrigerated (unpreserved) had higher pH and ammonium, because of the hydrolysis of urea from bacterial urease action and release of hydroxyl and ammonium ions. Urinary uric acid and citrate were significantly reduced, probably due to bacterial enzymatic degradation. Moreover, urinary calcium, magnesium and phosphorus declined, owing to the precipitation of calcium phosphate and magnesium phosphate at high pH. However, urinary oxalate increased probably due to ascorbic acid conversion to oxalate. Sodium, potassium and sulfate were unaltered.

The above tests were performed with well-established (well-known) techniques. Urinary pH was measured on a pH meter, uric acid by uricase technique, sodium and potassium by flame photometry, ammonium by colorimetric method using nitroferricyanide, citrate by the enzymatic method using citrate lyase, calcium and magnesium by atomic absorption spectrophotometry, phosphorus by the colorimetric method using molybdate, oxalate by ion chromatography, and sulfate by precipitation as barium sulfate.

Ability of thymol to prevent infection and provide reliable analysis of pH, uric acid, sodium and potassium In 12 urine samples, thymol was added before bacterial contamination and incubation at high temperature (as in previous study of Table 1). Results were compared with those of corresponding aliquots kept fresh under refrigeration (without bacterial inoculation) (Table 2).

TABLE 2

| Ability of Thymol to Prevent Changes in pH Uric Acid Citrate, Sodium, and Potassium | | |
|---|---|---|
| | Fresh | Thymol |
| pH | 6.41 ± 0.57 | 6.47 ± 0.55 |
| Uric Acid (mg/l) | 246 ± 82 | 240 ± 82 |
| Sodium (meq/l) | 70 ± 32 | 70 ± 32 |
| Potassium (meq/l) | 39 ± 26 | 37 ± 25 |
| Citrate (mg/l) | 320 ± 253 | 325 ± 250 |

Values are presented as mean ± SD.

Thus, the addition of thymol prevented the rise in urinary pH and the fall in urinary uric acid and citrate. Moreover, urinary sodium and potassium were kept unchanged.

Ability of thymol+hydrochloric acid+boric acid to prevent changes in urinary ammonium, citrate, magnesium, phosphorus, oxalate and sulfate In aliquots from 12 urine samples, thymol, hydrochloric acid and boric acid were added. Specimens were then inoculated and incubated as before. Results were compared with those of corresponding aliquots which had been kept refrigerated without bacterial inoculation (Table 3).

TABLE 3
Effect of Preservation with Thymol, Hydrochloric Acid and Boric Acid

|  | Fresh | Preserved |
|---|---|---|
| Ammonium (mg/l) | 204 ± 113 | 181 ± 70 |
| Citrate (mg/l) | 310 ± 103 | 303 ± 115 |
| Calcium (mg/l) | 98 ± 39 | 100 ± 39 |
| Magnesium (mg/l) | 52 ± 25 | 52 ± 24 |
| Phosphorus (mg/l) | 387 ± 193 | 396 ± 195 |
| Oxalate (mg/l) | 18.8 ± 9.0 | 18.5 ± 6.1 |
| Sulfate (mmoles/l) | 11.2 ± 3.2 | 9.9 ± 3.0 |

Values are presented as mean ± SD.

Thus, the addition of thymol, hydrochloric acid and boric acid before bacterial contaminatin and incubation prevented changes in ammonium, citrate, calcium, magnesium, phosphorus, oxalate and sulfate.

Accurate estimation of urinary total volume from lithium dilution

Twelve subjects were asked to divide urine sample after each void equally into two portions over 24-hours. One portion was collected in a container containing lithium chloride. The other equal portion was collected in another container without lithium. The total volume, estimated from the lithium dilution in the first container, was compared with the directly measured volume in the second container. There was excellent correspondence (1083±294 SD ml directly measured vs. 1077±283 ml estimated). For the above, in order to estimate total amount of urine excreted each day (total volume), a known amount of lithium chloride is added to the urine container in which all urine passed over a 24-hour period is collected. After thorough mixing, the concentration of lithium in urine is determined using atomic absorption spectrophotometer. From this lithium concentration, total volume of urine can be calculated, since total volume is inversely proportional to the lithium concentration.

Actual embodiments of urine collection and preservation

The following method is an example of an effective urine collection and preservation system, and is not meant to include minor modifications in design or amounts of materials used. The materials include a urine collection container and two small containers for shipment. The collection container is a 4-liter plastic bottle (wide-mouth) which has a sponge block embedded with 2 g of lithium chloride and 900 mg of thymol. The shipment containers are two 30 ml plastic bottles, one plain and the other packed with glass wool containing 0.6 g of boric acid and 2.5 ml of 6N hydrochloric acid.

The patient collectsurine over a 24-hour period in the collection container while the container is kept in the refrigerator or ice chest. Immediately after completion of collection, 30 ml aliquots of well-mixed 24-hour specimen are transferred to shipment containers, which are then mailed without refrigeration or freezing to the laboratory for analysis of stone-forming risks (Table 4).

TABLE 4

| Recommended Analysis | |
|---|---|
| Thymol + Lithium | Thymol + Lithium + HCl + Boric Acid |
| Total volume | Ammonium |
| pH | Citrate |
| Uric Acid | Calcium |
| Sodium | Magnesium |
| Potassium | Phosphorus |
| Citrate | Oxalate |
|  | Sulfate |

Citrate may be analyzed in either preservation system.

Graphic display of stone-forming risks

The above urinary measures were divided into metabolic and environmental factors. Metabolic factors included calcium, oxalate, uric acid, citrate and pH. This categorization recognizes important pathogenetic role in stone formation of hypercalciuria, hyperoxaluria, hyperuricosuria, hypocitraturia and abnormally high or low urinary pH. Environmental factors included total volume, sodium, sulfate, phosphorus and magnesium. Using these values, urinary saturations of calcium oxalate, brushite, monosodium urate, struvite and uric acid were derived from activity products (for the first four stone-forming salts) and from the concentration of undissociated uric acid (for uric acid). They represented physicochemical factors.

For each risk factor, upper or lower normal limit was established. These limits for metabolic and environmental factors determined from normal population by the inventor were: calcium<250 mg/day, oxalate<45 mg/day, uric acid<700 mg/day, sodium<200 meq/day, sulfate<30 mmoles/day, phosphorus<1100 mg/day, citrate>320 mg/day, pH>5.5 and <7.0, total volume>2 liters/day and magnesium>60 mg/day. For the derivation of upper normal limits for physicochemical factors, activity product of calcium oxalate, brushite, monosodium urate and struvite and the concentration of undissociated uric acid were calculated from urine samples obtained from 41 normal subjects without stones by the inventor. The mean values of activity products were $7.30 \times 10^{-9} M^2$ for calcium oxalate, $2.35 \times 10^{-7} M^2$ for brushite, $3.80 \times 10^{-5} M^2$ for monosodium urate, and $4.69 \times 10^{-15} M^2$ for struvite. The mean value in normal subjects for the concentration of undissociated uric acid was $2.72 \times 10^{-5} M$. The upper normal limit was taken to be twice the mean value of activity product for calcium oxalate, brushite, and monosodium urate, and twice the mean value of the concentration of undissociated uric acid. For struvite, the upper normal limit was taken as 75 times the mean activity product. For each urine sample to be tested, physicochemical risk factors were expressed as relative supersaturation, calculated as the ratio of activity product (or concentration of undissociated uric acid) in the particular urine sample and the corresponding mean activity product (or undissociated uric acid) from normal subjects.

In order to provide a visual display of all available data in a single report, each factor was assigned a vertical line with linear or logarithmic scale. Risk factors were grouped into metabolic, environmental or physicochemical risks. A horizontal line intersecting each vertical scale at approximate midpoint represented upper or lower normal limit. The direction of increasing values was appropriate adjusted, such that values below the horizontal line represented normal values (reduced risk) and above the line abnormal values (increased risk). For metabolic and environmental risks, values above the horizontal line indicated occurrence of metabolic or environmental disturbances. For physicochemical risks, values above the horizontal line represented relative supersaturation (greater degree of supersaturation than in normal subjects) with respect to specified stone-forming salt(s).

A computer program has been devised to format and display urinary risk factors. From the entry of actual data derived from urine collection and preservation described previously, the program calculates activity products and undissociated uric acid as well as relative supersaturation.

Such a graphic display has a diagnostic value as well as practical utility in assessing response to treatment reflecting accurate values achieved by the present invention. It has diagnostic importance because characteristic environmental and metabolic derangements can be readily identified. The efficacy of therapeutic program can be assessed since effective treatment has been shown to convert risk factors from increased risk toward reduced risk.

A Search of the prior art failed to locate any relevant prior art. Patents located during the search include Deindoerfer U.S. Pat. No. 4,393,466, Hambleton et al. Pat. No. 3,965,477, and Quarton U.S. Pat. No. 4,074,281.

I claim:

1. A method for maintaining a timed urine specimen for subsequent laboratory analysis from the time of collection of said specimen until said specimen is analyzed, said method comprising the steps of:
   a. Providing a collection container having sufficient volume to accommodate the total volume of urine specimens to be accumulated from each voiding during a timed interval, said collection container having disposed therein predetermined amounts of thymol and lithium chloride;
   b. Pouring the urine specimen collected from each voiding during said interval into said collection container so as to accumulate the specimens collected from each voiding;
   c. Maintaining the accumulated urine specimens collected from each voiding during said interval in said collection container until the conclusion of said interval;
   d. Providing a second container having substantially less volume than said collection container, said second container having disposed therein predetermined amounts of boric acid and hydrochloric acid;
   e. Transferring a first aliquot of the total volume of urine specimens collected during said interval into said second container;
   f. Providing a third container having substantially less volume than said collection container;
   g. Transferring a second aliquot of the total volume of urine specimens collected during said interval into said third container; and
   h. Transporting said second container, containing said first aliquot, and said third container, containing said second aliquot, to said laboratory for analysis.

2. The method of claim 1 wherein said collection container is a wide-mouth plastic bottle.

3. The method of claim 1 wherein said collection container has a volume of up to about four liters.

4. The method of claim 3 wherein said collection container has a volume of about four liters.

5. The method of claim 1 wherein said predetermined amount of thymol ranges from about 300 mg to about 2 g.

6. The method of claim 5 wherein said predetermined amount of thymol ranges from about 600 mg to about 1200 mg.

7. The method of claim 6 wherein said predetermined amount of thymol is about 900 mg.

8. The method of claim 1 wherein said predetermined amount of lithium chloride ranges from about 375 mg to about 10 g.

9. The method of claim 8 wherein said predetermined amount of lithium chloride ranges from about 1 g to about 3 g.

10. The method of claim 9 wherein said predetermined amount of lithium chloride is about 2 g.

11. The method of claim 1 wherein said collection container is maintained in a cool environment during said interval.

12. The method of claim 11 wherein said cool environment is a refrigerator.

13. The method of claim 11 wherein said cool environment is an ice chest.

14. The method of claim 1 wherein the volume of said first aliquot is about 30 ml.

15. The method of claim 1 wherein the volume of said second aliquot is about 30 ml.

16. The method of claim 1 wherein said second container is a plastic bottle.

17. The method of claim 1 wherein said second container has a volume of about 30 ml.

18. The method of claim 1 wherein said third container has a volume of about 30 ml.

19. The method of claim 14 wherein said predetermined amount of boric acid ranges from about 0.3 g to about 1 g.

20. The method of claim 19 wherein said predetermined amount of boric acid ranges from about 0.4 g to about 0.7 g.

21. The method of claim 20 wherein said predetermined amount of boric acid is about 0.6 g.

22. The method of claim 14 wherein said predetermined amount of hydrochloric acid ranges from about 1 ml to about 4 ml of 6N hydrochloric acid.

23. The method of claim 22 wherein said predetermined amount of hydrochloric acid ranges from about 2 ml to about 4 ml of 6N hydrochloric acid.

24. The method of claim 23 wherein said predetermined amount of hydrochloric acid is about 2.5 ml of 6N hydrochloric acid.

25. The method of claim 14 wherein said predetermined amount of hydrochloric acid ranges from about 0.5 ml to about 2 ml of concentrated hydrochloric acid.

26. The method of claim 25 wherein said predetermined amount of hydrochloric acid is about 1 ml of concentrated hydrochloric acid.

27. The method of claim 1 wherein said thymol and said lithium chloride are maintained in a sponge block disposed inside said collection container prior to the introduction of urine into said collection container.

28. The method of claim 1 wherein said thymol and said lithium chloride are maintained in glass wool disposed inside said collection container prior to the introduction of urine into said collection container.

29. The method of claim 1 wherein said boric acid and said hydrochloric acid are maintained in glass wool disposed inside said second container prior to the introduction of urine into said second container.

30. The method of claim 1 wherein said timed interval is 24 hours.

31. The method of claim 1 wherein said third container is a plastic bottle.

32. Apparatus for receiving and maintaining a timed urine specimen for subsequent laboratory analysis from the time of collection of said specimen until said specimen is analyzed, said apparatus comprising:
 a. A collection container having sufficient volume to accommodate the total volume of urine specimens to be accumulated from each voiding during a timed interval, said collection container having disposed therein predetermined amounts of thymol and lithium chloride;
 b. A second container having substantially less volume than said collection container, said second cintainer having disposed therein predetermined amounts of boric acid and hydrochloric acid; and
 c. A third container having substantially less volume than said collection container.

33. The apparatus of claim 32 wherein said collection container is a wide-mouth plastic bottle.

34. The apparatus of claim 32 wherein said collection container has a volume of up to about four liters.

35. The apparatus of claim 34 wherein said collection container has a volume of about four liters.

36. The apparatus of claim 32 wherein said predetermined amount of thymol ranges from about 300 mg to about 2 g.

37. The apparatus of claim 36 wherein said predetermined amount of thymol ranges from about 600 mg to about 1200 mg.

38. The apparatus of claim 37 wherein said predetermined amount of thymol is about 900 mg.

39. The apparatus of claim 32 wherein said predetermined amount of lithium chloride ranges from about 375 mg to about 10 g.

40. The apparatus of claim 39 wherein said predetermined amount of lithium chloride ranges from about 1 g to about 3 g.

41. The apparatus of claim 40 wherein said predetermined amount of lithium chloride is about 2 g.

42. The apparatus of claim 32 wherein said second container is a plastic bottle.

43. The apparatus of claim 32 wherein said second container has a volume of about 30 ml.

44. The apparatus of claim 32 wherein said third container is a plastic bottle.

45. The apparatus of claim 32 wherein said third container has a volume of about 30 ml.

46. The apparatus of claim 32 wherein said predetermined amount of boric acid ranges from about 0.3 g to about 1 g.

47. The apparatus of claim 46 wherein said predetermined amount of boric acid rages from about 0.4 g to about 0.7 g.

48. The apparatus of claim 47 wherein said predetermined amount of boric acid is about 0.6 g.

49. The apparatus of claim 32 wherein said predetermined amount of hydrochloric acid ranges from about 1 to about 4 ml of 6N hydrochloric acid.

50. The apparatus of claim 49 wherein said predetermined amount of hydrochloric acid ranges from about 2 ml to about 4 ml of 6N hydrochloric acid.

51. The apparatus of claim 50 wherein said predetermined amount of hydrochloric acid is about 2.5 ml of 6N hydrochloric acid.

52. The apparatus of claim 32 wherein said predetermined amount of hydrochloric acid ranges from about 0.5 ml to about 2 ml of concentrated hydrochloric acid.

53. The apparatus of claim 52 wherein said predetermined amount of hydrochloric acid is about 1 ml of concentrated hydrochloric acid.

54. The apparatus of claim 32, further comprising a sponge block disposed inside said collection container, said sponge block having said thymol and said lithium chloride disposed therein.

55. The apparatus of claim 32, further comprising glass wool disposed inside said collection container, said glass wool having said thymol and said lithium chloride disposed therein.

56. The apparatus of claim 32, further comprising glass wool disposed inside said second container, said glass wool having said boric acid and said hydrochloric acid disposed therein.

57. The apparatus of claim 32 wherein said timed interval is 24 hours.

* * * * *